United States Patent
Thoen (10) Patent No.: US 10,111,590 B2
(45) Date of Patent: Oct. 30, 2018

(54) HEALTH MONITORING DEVICE

(71) Applicant: NXP B.V., Eindhoven (NL)

(72) Inventor: Steven Mark Thoen, Leuven (BE)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 14/836,703

(22) Filed: Aug. 26, 2015

(65) Prior Publication Data

US 2017/0055834 A1 Mar. 2, 2017

(51) Int. Cl.
*A61B 5/00* (2006.01)
*A61F 13/42* (2006.01)

(52) U.S. Cl.
CPC ............ *A61B 5/002* (2013.01); *A61B 5/0004* (2013.01); *A61B 5/6804* (2013.01); *A61B 5/6807* (2013.01); *A61B 5/6808* (2013.01); *A61B 5/6891* (2013.01); *A61B 5/6892* (2013.01); *A61B 5/746* (2013.01); *A61B 2562/029* (2013.01); *A61B 2562/0247* (2013.01); *A61B 2562/0257* (2013.01); *A61B 2562/0261* (2013.01); *A61B 2562/0271* (2013.01); *A61F 13/42* (2013.01)

(58) Field of Classification Search
CPC ... A61B 5/6808; A61B 5/6891; A61B 5/6892; A61B 5/746; A61B 2562/0247; A61B 2562/0257; A61B 2562/0261; A61B 2562/0271; A61B 2562/029; A61B 5/002; A61B 5/6807
See application file for complete search history.

(56) References Cited

U.S. PATENT DOCUMENTS

| | | | | |
|---|---|---|---|---|
| 6,372,951 B1 * | 4/2002 | Ter-Ovanesyan | | |
| | | | | A61B 5/04884 |
| | | | | 600/373 |
| 6,685,634 B1 * | 2/2004 | Fry | ........ | A61B 5/0002 |
| | | | | 128/903 |
| 6,774,800 B2 * | 8/2004 | Friedman | ........ | A61B 5/0002 |
| | | | | 340/572.5 |
| 6,916,968 B2 * | 7/2005 | Shapira | ........ | A61F 13/42 |
| | | | | 340/571 |
| 7,141,715 B2 * | 11/2006 | Shapira | ........ | A61F 13/42 |
| | | | | 604/361 |
| 8,196,809 B2 * | 6/2012 | Thorstensson | ........ | A61F 13/42 |
| | | | | 235/375 |
| 9,119,748 B2 * | 9/2015 | Abraham | ........ | A61F 13/42 |
| 9,278,033 B2 * | 3/2016 | Abraham | ........ | A61F 13/42 |
| 9,420,952 B2 * | 8/2016 | Paquet | ........ | A61B 5/0008 |

(Continued)

FOREIGN PATENT DOCUMENTS

| | | |
|---|---|---|
| DE | 20 2013 101 920 U1 | 5/2013 |
| DE | 202013101920 U1 | 8/2014 |
| JP | 11216154 | 8/1999 |

OTHER PUBLICATIONS

Simavita; Product Info; http://simavita.com/product-sales/our-produt/; retrieved from the Internet Jul. 31, 2015.

(Continued)

*Primary Examiner* — Quan-Zhen Wang
*Assistant Examiner* — Rajsheed Black-Childress (57) ABSTRACT

One example discloses a health monitoring device, including: a communications circuit configured to receive a set of health sensor data based on a body surface; and a near-field antenna, coupled to the circuit, and conformally coupled to the body surface.

20 Claims, 7 Drawing Sheets

(56) References Cited

U.S. PATENT DOCUMENTS

| | | | |
|---|---|---|---|
| 2002/0070868 A1 | 6/2002 | Jeutter et al. | |
| 2004/0036484 A1* | 2/2004 | Tamai | A61F 13/42 324/663 |
| 2004/0220538 A1* | 11/2004 | Panopoulos | A61F 13/42 604/361 |
| 2004/0230172 A1 | 11/2004 | Shapira | |
| 2007/0268144 A1* | 11/2007 | Dobosz | G06K 7/0008 340/572.8 |
| 2008/0074274 A1 | 3/2008 | Hu et al. | |
| 2008/0266123 A1 | 10/2008 | Ales et al. | |
| 2011/0022411 A1 | 1/2011 | Hjelm et al. | |
| 2013/0069444 A1 | 3/2013 | Waffenschmidt et al. | |
| 2013/0076509 A1 | 3/2013 | Ahn | |
| 2013/0123726 A1 | 5/2013 | Yu et al. | |
| 2013/0161380 A1 | 6/2013 | Joyce et al. | |
| 2014/0358099 A1* | 12/2014 | Durgin | A61F 13/42 604/361 |

OTHER PUBLICATIONS

"Tena Identifi, a new continence care technology by SCA, is in the final stages of clearance for United States introduction" retrieved from the internet http://www.sca.com/en/us/Press/Press-Release/Archive/2014/TENA-Identifi-a-new-continence-care-technology-by-SCA-is-in-the-final-stages-of-clearance-for-United-States-introduction/ Jul. 31, 2015; 4 pages (May 21, 2014).

Ziai, M. A. et al; "Smart RFID Tag for Diaper Moisture Detection"; Institute of Engineering and Technology; 8 pages (2014).

* cited by examiner

HEALTH MONITORING DEVICE

The present specification relates to systems, methods, apparatuses, devices, articles of manufacture and instructions for body monitoring.

Collection of data from wearable devices can be a challenge, particularly for single use, disposable devices in a hospital or care facility. For example, sensors for incontinence monitoring provides benefits for both a patient (better profiling, avoidance of leaks, personalized care . . . ) and caregiver (better hygiene, avoidance of leaks . . . ).

Also, adding an active device inside a disposable diaper requires some form of disposable battery, adding to the diaper's total cost and causing a higher environmental impact due to the battery chemicals and metal.

An active device could be plugged into the diaper and then unplugged after use of the diaper, however this requires additional handling by a caregiver and raises hygiene concerns.

Passive (i.e. non-powered) circuits inside a diaper may be used in conjunction with a mobile handheld tag reader; however, this solution requires manual scanning and does not allow for an automatic alarm function since it still requires the caregiver to perform regular manual checks using the mobile tag reader.

SUMMARY

According to an example embodiment, a health monitoring device, comprising: a communications circuit configured to receive a set of health sensor data based on a body surface; and an near-field antenna, coupled to the circuit, and configured to be conformally coupled to the body surface.

In another example embodiment, the body surface has a maximum cross-section; and the near-field antenna has at least one spatial dimension greater than or equal to the maximum cross-section.

In another example embodiment, the near-field antenna is configured to surround at least one of: the body surface, a waist, a torso, an arm, a leg, a lower body region, a wound, a chest, or a head.

In another example embodiment, the near-field antenna includes at least one of: an air core or a ferrite core.

In another example embodiment, a shape of the near-field antenna is at least one of: a solenoid, a dipole, a closed shape, a spiral or a loop.

In another example embodiment, the near-field antenna includes a detachable electrical coupling between a first and second antenna segments.

In another example embodiment, further including a single-use structure having a set of sensors configured to generate the set of health sensor data based on the body surface; and the single-use structure includes only externally powered passive circuits.

In another example embodiment, the near-field antenna is embedded in at least one of: an item of clothing, a sock, an undergarment, a diaper, a bandage, a tape, a splint, a cast, a bed sheet, a cushion, or a covering.

In another example embodiment, at least one of the sensors is: a humidity sensor, a temperature sensor, a pressure sensor, a gas sensor, molecular sensor, a microbial sensor, a stress sensor, a position sensor, or a proximity sensor.

In another example embodiment, further including: a re-useable structure having a near-field reader configured to process the set of health sensor data based on the body surface.

In another example embodiment, the near-field antenna is embedded in at least one of: an item of clothing, a belt, a shirt, pants, a chest strap, a necklace, a bed, a chair, or a piece of furniture.

In another example embodiment, further comprising a wireless antenna configured to transmit the set of health sensor data using at least one of: a wifi signal, a cellular signal, a Bluetooth signal, or a zigbee signal.

In another example embodiment, the re-useable structure is configured to transmit an alarm signal over the wireless antenna in response to a threshold value within the set of health sensor data.

In another example embodiment, a first near-field antenna in the re-useable structure is configured to communicate with a second near-field antenna in a single-use structure having a set of sensors configured to generate the set of health sensor data based on the body surface; and the single-use structure is wholly powered by a near-field signal from the re-useable structure.

In another example embodiment, the first near-field antenna is spatially positioned with respect to the second near-field antenna so as to maximize a coupling factor between the first and second near-field antennas.

In another example embodiment, the near-field antenna has at least one spatial dimension greater than or equal to a cross-section of the body surface.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Combining a re-usable active health monitoring device with a single-use passive health monitoring device, wherein both devices communicate using an NFC or other near-field signal would enable the low-cost single-use device to be disposed of, while relying on the re-usable device for relaying patient health data from the single-use device sensors to a remote caregiver.

For example, by using health monitoring devices (e.g. wearable devices such as a belt or a necklace) which contain an active (i.e. self-powered) NFC (or near-field) reader in conjunction with a passive NFC circuit embedded in a single-use structure (e.g. an incontinence diaper) with various sensors, remote patient monitoring is enabled in an inexpensive and convenient manner.

Patient and/or caregiver intervention is not required since the re-usable active health monitoring device autonomously reads out sensor information (e.g. a humidity level) from the NFC-powered sensors and circuits in the single-use structure (e.g. diaper). The re-usable active health monitoring device then forwards this set of health sensor data through an additional wireless interface (e.g. wifi, zigbee, bluetooth, etc.) to a remote caregiver.

Since the sensors in the single-use structure are powered from the NFC field, no battery is required and a total cost of the single-use structure is minimized. Additionally, no batteries need to be disposed of, which reduces the environmental impact as well.

In one set of example embodiments, the re-usable active health monitoring device with the reader can be embedded into articles of clothing worn by the patient and/or user (e.g. a sock, a belt, a neckless, a wallet, pants, shirt, shoes, and additional undergarments). In alternate example embodiments, the reader could be embedded into articles and structures nearby by the patient (e.g. a chair, a bed, a table, a cup, a plate).

Figure 1:
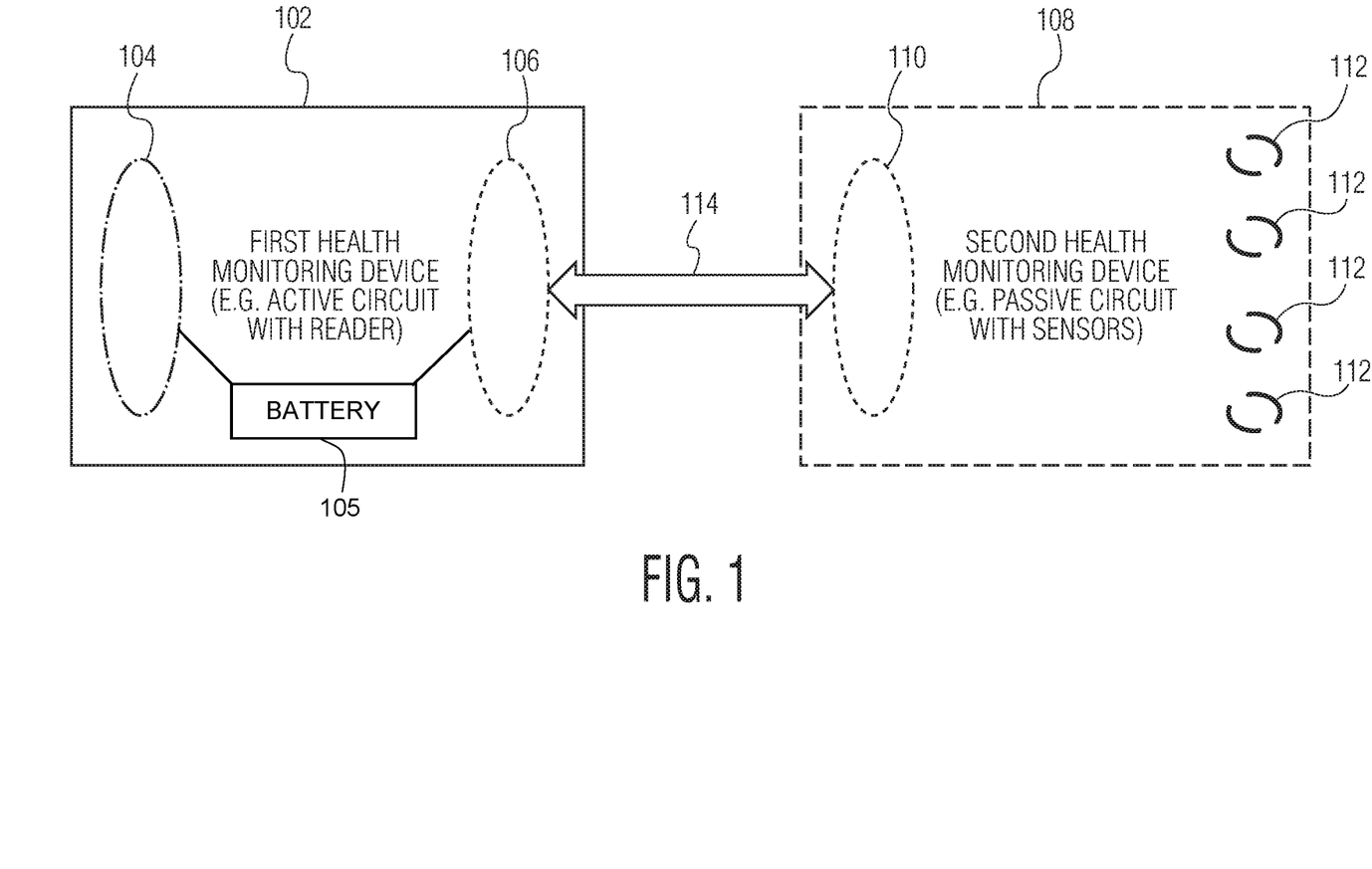
FIG. 1 is an example set of health monitoring devices.

FIG. 1 is an example set of health monitoring devices. A first active health monitoring device 102 (e.g. a re-useable structure) includes a wireless antenna 104, a first NFC antenna 106, an NFC reader (not shown), a battery 105, and various other communication, logic and/or memory circuits (not shown). This re-useable structure 102 includes at least one internally powered active circuit. In example embodiments, the NFC antenna 106 is embedded in at least one of: an item of clothing, a belt, a shirt, pants, a chest strap, a necklace, a bed, a chair, or a piece of furniture.

Also in example embodiments, the wireless antenna 104 is configured to transmit an alarm and/or a set of health sensor data using at least one of: a wifi signal, a cellular signal, a Bluetooth signal, or a zigbee signal. This information can be received by a variety of devices including: a local Wifi hotspot, a smartphone, a server, or a cellular node, thereby enabling caregivers to be notified and respond to a patient condition indicated by the set of health sensor data.

A second passive health monitoring device 108 (e.g. single-use structure) includes a second NFC antenna 110, a set of sensors 112 for providing a set of health sensor data from or within sensing distance of a body surface, and various other communication, logic and/or memory circuits (not shown). In one example, the passive single-use structure 108 includes only externally powered passive circuits. In various examples, the second NFC antenna 110 can be embedded in: an item of clothing, a sock, an undergarment, a diaper, a bandage, a tape, a splint, a cast, a bed sheet, a cushion, or a covering.

Also, the set of sensors 112 can include: a humidity sensor, a temperature sensor, a pressure sensor, a gas sensor, a molecular sensor, a microbial sensor, a stress sensor, a position sensor, or a proximity sensor.

The first and second health monitoring devices 102, 108 communicate using the first and second NFC antennas 106, 110 based on coupling factor 114. In one example, the second passive health monitoring device 108 is periodically powered and queried by the first active health monitoring device 102 using an NFC reader integrated into the device 102.

The communications circuits in either of the health monitoring devices 102, 108 are configured to receive the set of health sensor data based on a body surface (e.g. any location on or within sensing distance of a person's body). In one example embodiment, the second health monitoring device 108 collects the set of health data and transmits the data to the first health monitoring device 102 via NFC.

The first health monitoring device 102 communication circuit receives the health data via NFC and relays it via a wireless signal to a caregiver. In one example, the first health monitoring device 102 is configured to transmit an alarm signal over the wireless antenna in response to a threshold value within the set of health sensor data.

For maximum NFC coupling between the first and second NFC antennas 106, 110, these antennas 106, 110 and the re-useable and/or single-use structures they and the health monitoring devices 102, 108 are embedded in, are conformally coupled to the body surface to be monitored. Conformally coupled is herein defined as adapting to a set of body surface contours, such that the antenna geometry either closely or approximately takes a shape which mimics the body surface. Some examples of this conformal coupling to a body surface are shown in FIGS. 2A, 2B, 4 and 5. The degree of conformality can vary from a "snug fit" to a "loose draping", each having an effect on the coupling factor between the antennas 106, 110.

Figure 2A:
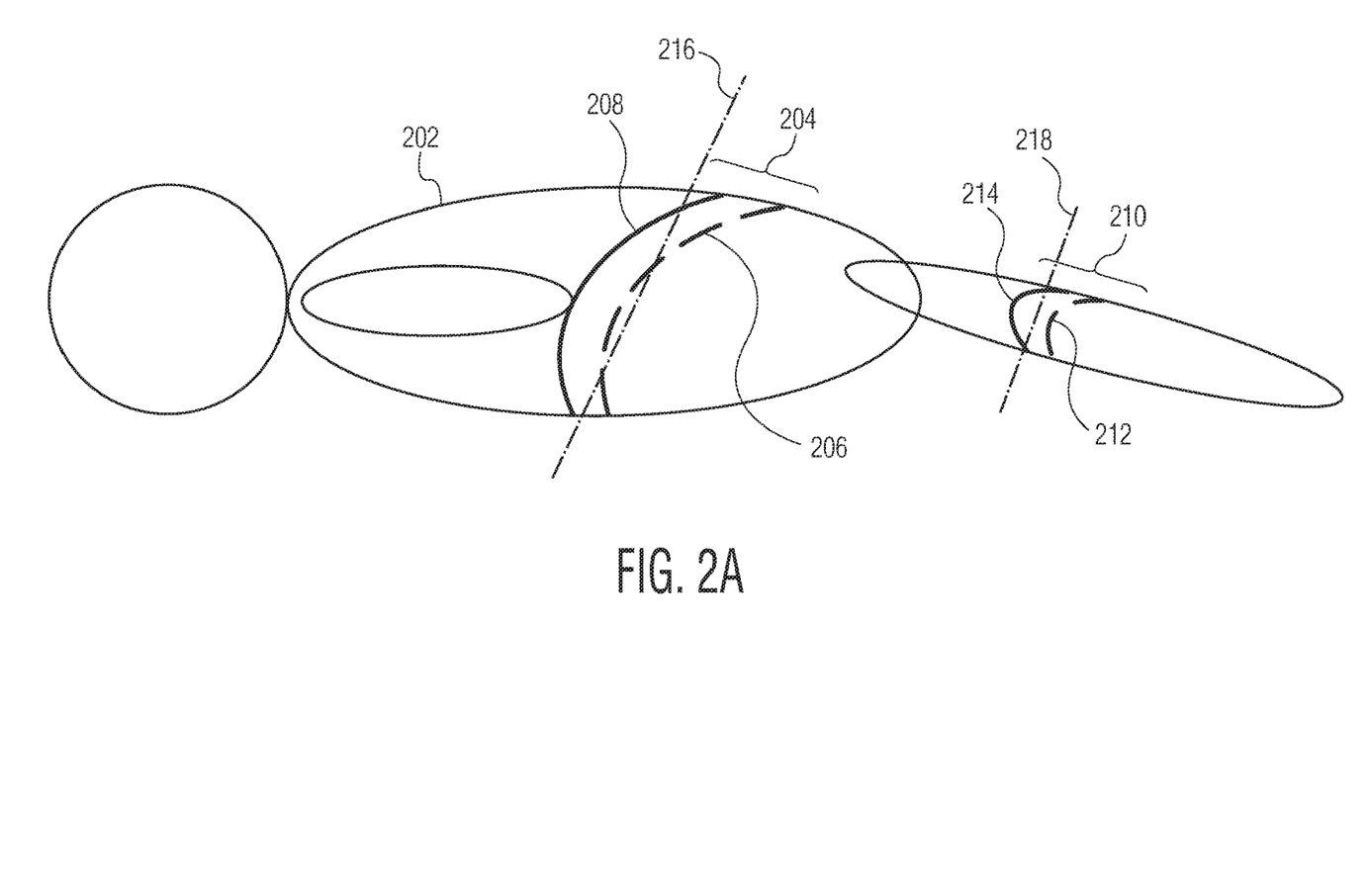
FIG. 2A is an example set of health monitoring devices applied to a set of body surfaces.
Figure 2B:
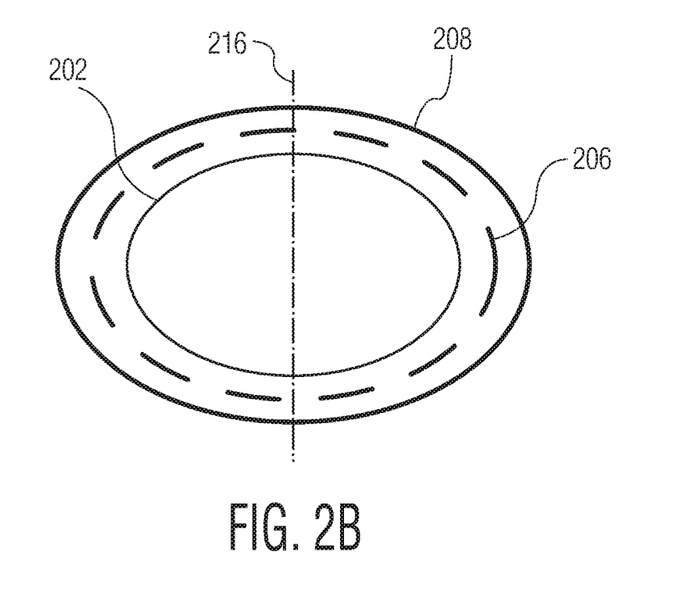
FIG. 2B is an example first cross-section.

In one example embodiment the NFC antennas 106, 110 have at least one spatial dimension greater than or equal to a cross-section of the body surface, as shown in FIGS. 2A and 2B, and are positioned so as to maximize a coupling factor between the first and second NFC antennas 106, 110.

FIG. 2A is an example set of health monitoring devices applied to a set of body surfaces. Shown is an idealized human body 202. Attached to the body 202 is a first set of health monitoring devices 204, show to encircle a torso of the body 202. The first monitoring devices 204 include a single-use structure 206 (e.g. a diaper) and a re-useable structure 208 (e.g. a reader embedded in a belt).

Similarly, attached to the body 202 is a second set of health monitoring devices 210, show to encircle a leg of the body 202. The second monitoring devices 210 include a single-use structure 212 (e.g. a bandage) and a re-useable structure 214 (e.g. a reader embedded in an elastic leg band).

FIG. 2B is an example first cross-section 216. The first set of health monitoring devices 204 have a cross-sectional diameter equal to or greater than a cross-sectional diameter of the body's 202 torso. Particularly, the NFC antennas embedded in the single-use structure 206 and re-useable structure 208 are sufficiently large and sufficiently close to ensure an adequate coupling factor for NFC communication of a set of health data between the structures 206, 208.

Figure 2C:
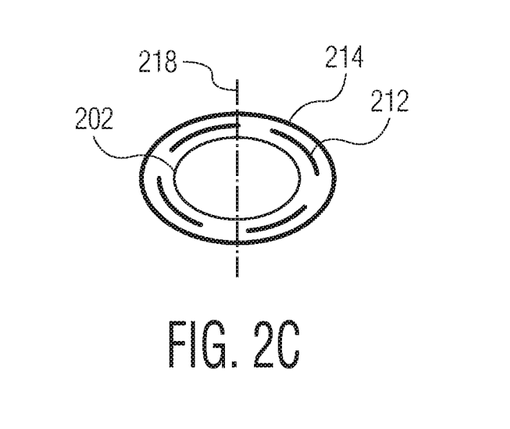
FIG. 2C is an example second cross-section.

FIG. 2C is an example second cross-section 218. The second set of health monitoring devices 210 have a cross-sectional diameter equal to or greater than a cross-sectional diameter of the body's 202 leg. Particularly, the NFC antennas embedded in the single-use structure 212 and re-useable structure 214 are sufficiently large and sufficiently close to ensure an adequate coupling factor for NFC communication of a set of health data between the structures 212, 214.

In other examples, health monitoring devices can partially or wholly encircle other portions of the body 202 such as: a waist, an arm, a lower body region, a surface wound, an internal organ, a chest, or a head.

Figure 3:
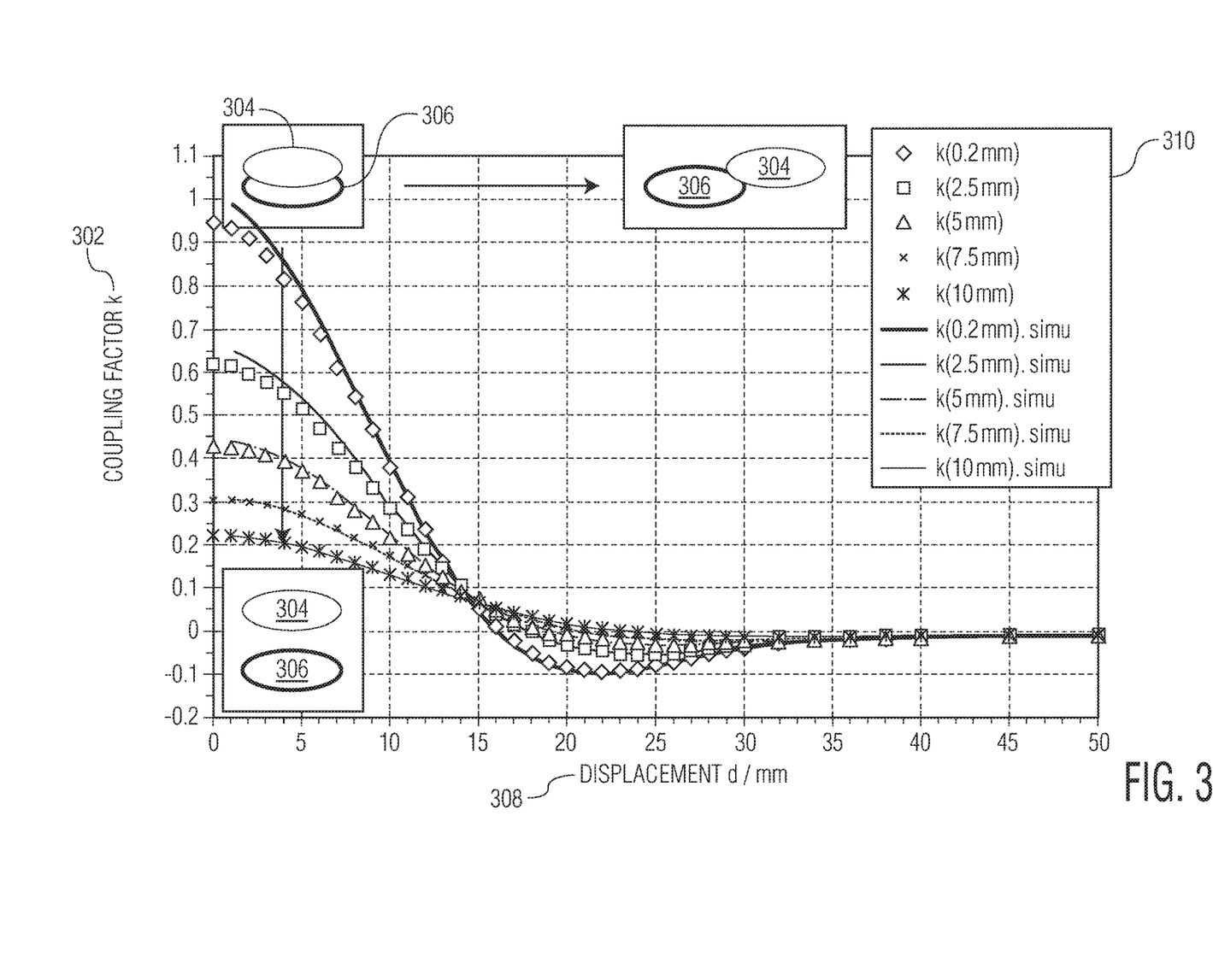
FIG. 3 is an example coupling factor between a first health monitoring device and a second health monitoring device.

FIG. 3 is an example coupling factor (k) 302 between a first health monitoring device 304 and a second health monitoring device 306. The coupling factor 302 is plotted compared to a displacement 308 (i.e. alignment of electromagnetic flux) between the devices 304, 306 and as compared to a distance 310 between the devices 304, 306. As shown in example FIG. 3, mutual coupling is a strong function of the distance 310 between NFC antennas in the devices 304, 306 and their relative alignment/displacement 308.

In one example, robust NFC communication between the devices 304, 306 occurs when a mutual coupling between the first health monitoring device 304 (e.g. reader antenna coil) and the second health monitoring device 306 (e.g. the sensor antenna coil) is at least 20%.

Figure 4:
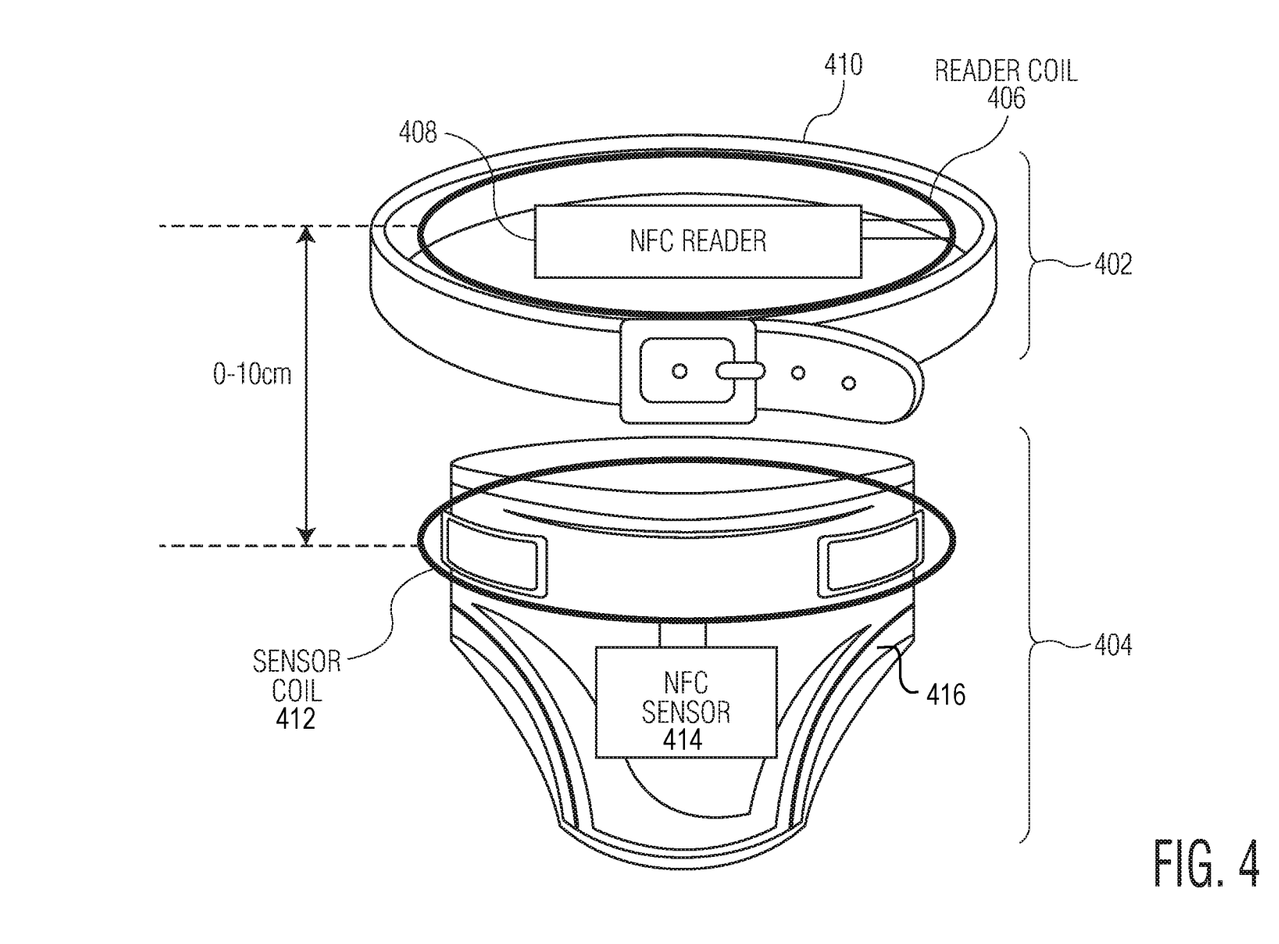
FIG. 4 is an example first health monitoring device embedded in a belt and a second health monitoring device embedded in a diaper, for incontinence monitoring.

FIG. 4 is an example first health monitoring device 402 embedded in a belt and a second health monitoring device 404 embedded in a diaper, for incontinence monitoring. The first health monitoring device 402 includes a reader coil 406 and NFC reader circuitry 408 embedded in a re-usable belt 410. The second health monitoring device 404 includes a sensor coil 412 and NFC sensor circuitry 414 embedded in an undergarment 416.

In this example, the first and second health monitoring devices 402, 404 are designed to work concentrically (e.g. belt coil 406 surrounds the diaper coil 412). These devices 402, 404 are designed so that there is a minimal distance between the coils 406, 412 and a nearly perfect angular alignment. Thus by integrating an NFC reader antenna in a specific form factor of a belt and by integrating a corresponding NFC sensor antenna in a top part of a diaper aligned to an axis of a human torso circumference, sufficient magnetic coupling between the reader and the NFC sensor is achieved.

A distance between the NFC reader coil 406 inside the belt and the NFC sensor coil 412 inside the diaper is typically less than 10 cm, if a diameter of both NFC antennas coils is typically 40 cm (corresponding to a 125 cm waist circumference) depending on age, weight and sex of the patient. From FIG. 3, this configuration results in a mutual coupling coefficient above 20% which should give robust NFC communication performance.

In an alternate example, the reader coil 406 includes a detachable electrical coupling at the belt buckle, which divides the reader coil 406 in to first and second antenna segments. When the belt buckle is clasped together the reader coil's 406 forms a continuous electrical antenna circuit.

In alternate embodiments, the reader coil 406 can be embedded in a necklace or collier. This provides good alignment in terms of displacement but creates a larger distance and a worse relative angular alignment. Alternatively, the reader coil 406 can be embedded in a chest strap could be considered as well.

Figure 5:
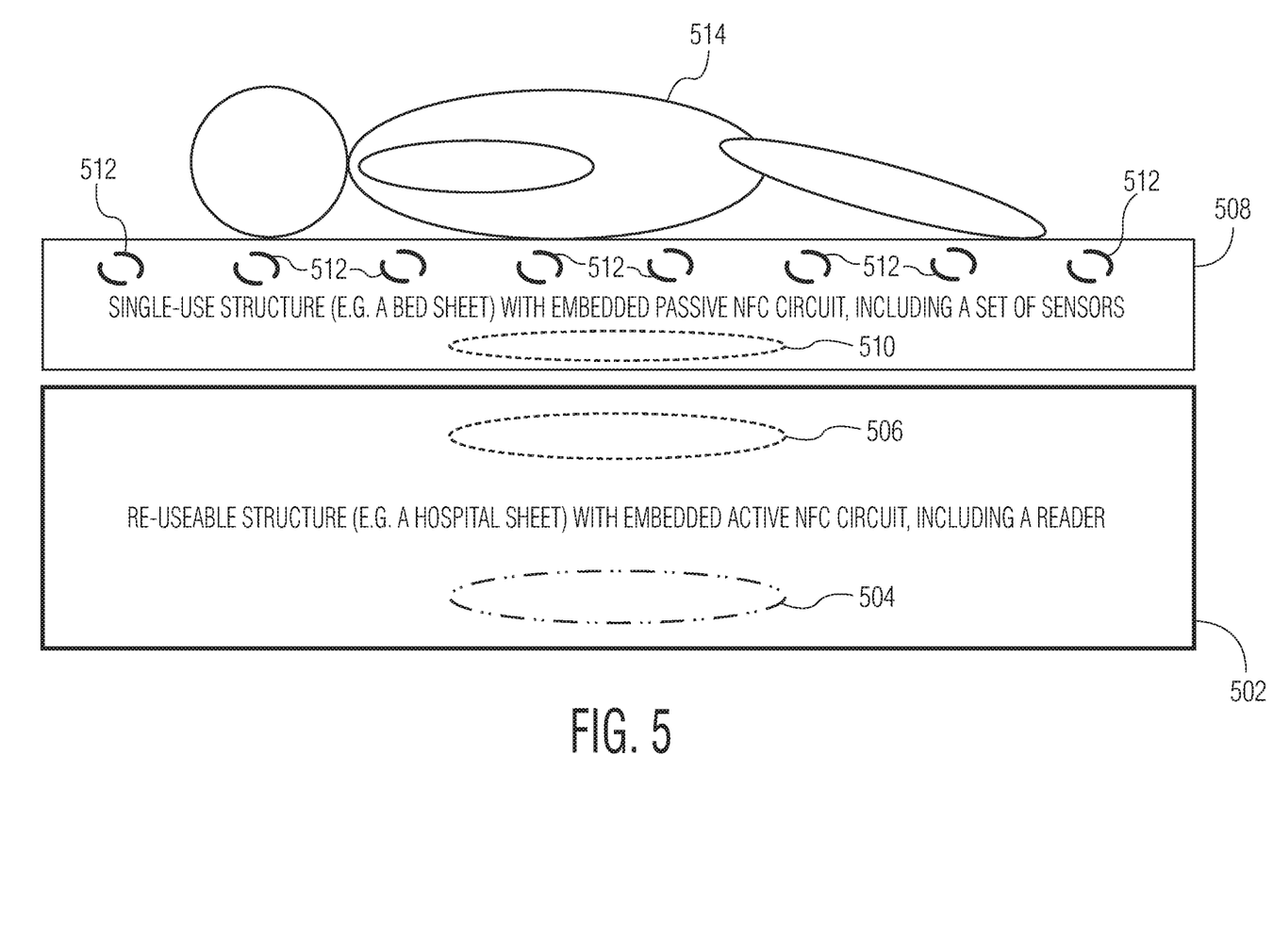
FIG. 5 is an example first health monitoring device embedded in a re-usable bed and a second health monitoring device embedded in a single-use or limited-use sheet, for incontinence monitoring.

FIG. 5 is an example active health monitoring device (e.g. structure) 502 embedded in a re-usable bed and a passive health monitoring device 508 embedded in a single-use or limited-use sheet, for incontinence monitoring, wound care, etc. The active health monitoring device 502 (e.g. re-useable structure) includes a wireless antenna 504, a first NFC antenna 506, an NFC reader (not shown), a battery (not shown), and various other communication, logic and/or memory circuits (not shown). This active health monitoring device 502 includes at least one internally powered active circuit.

The passive health monitoring device 508 (e.g. single-use or limited-use structure) includes a second NFC antenna 510, a set of sensors 512 for providing a set of health sensor data from a body 514 surface, and various other communication, logic and/or memory circuits (not shown). In one example, the passive single-use or limited-use structure 508 includes only externally powered passive circuits.

Figure 6A:
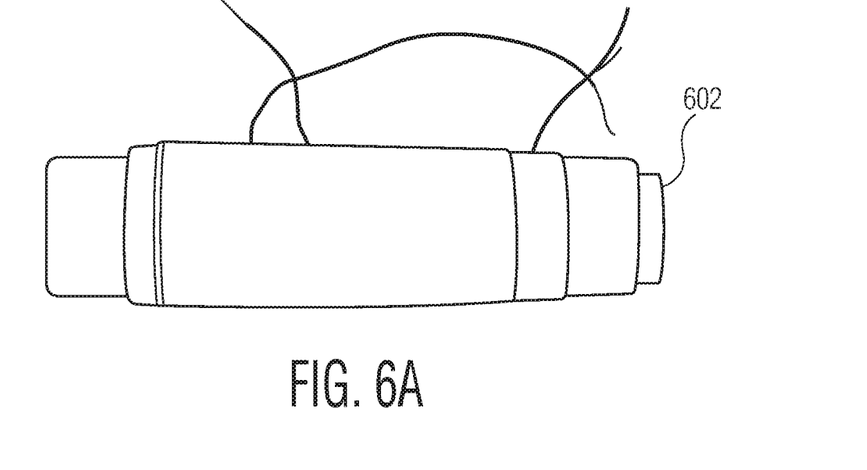
FIGS. 6A and 6B show example antenna designs embedded within a health monitoring device.
Figure 6B:
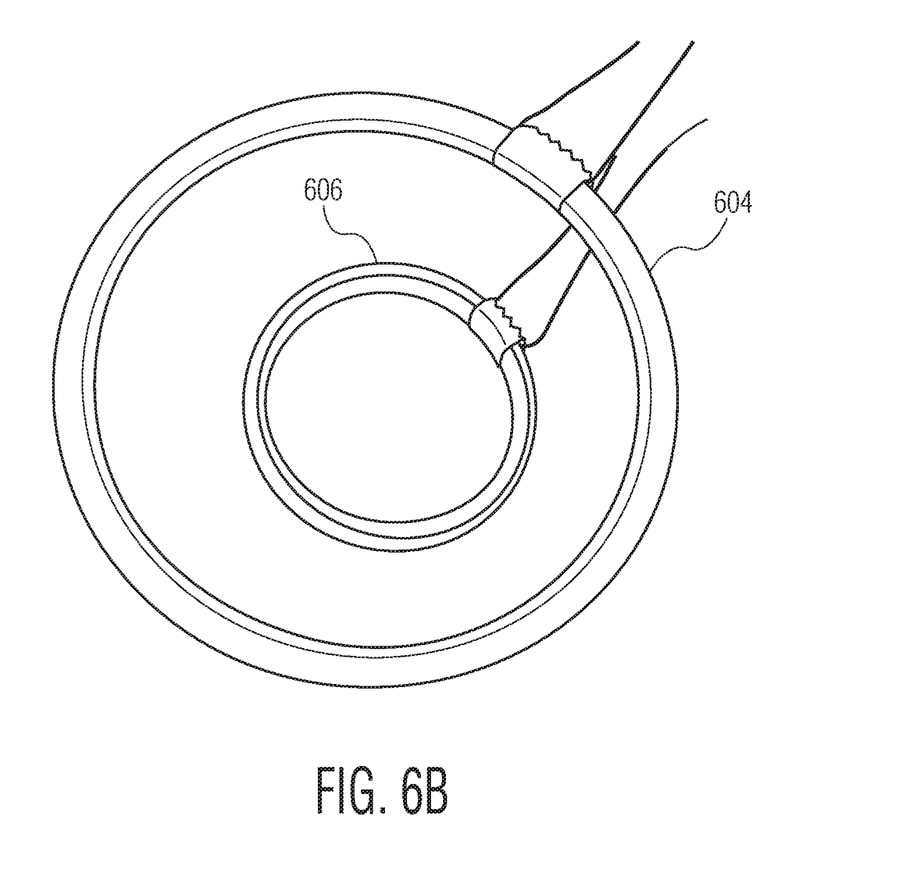

FIGS. 6A and 6B show example antenna designs embedded within a health monitoring device. FIG. 6A shows a ferrite core antenna coil 602 and FIG. 6B shows a first 604 and second 606 air core antenna coil. The air core antennas can at least have a shape which is at least one of: a dipole, a closed shape, a spiral or a loop.

In this specification, example embodiments have been presented in terms of a selected set of details. However, a person of ordinary skill in the art would understand that many other example embodiments may be practiced which include a different selected set of these details. It is intended that the following claims cover all possible example embodiments.

What is claimed is:

1. Health monitoring device, comprising:
    a single-use structure comprising:
        a set of sensors configured to generate a set of health sensor data based on a body surface;
        a communications circuit configured to receive the set of health sensor data based on the body surface; and
        a first near-field antenna, coupled to the circuit, and configured to be conformally coupled to the body surface, wherein the set of sensors and the first near-field antenna are externally powered passive circuits; and
    a re-useable structure, wherein the re-usable structure is wearable, the re-usable structure comprising:
        a near-field reader configured to process the set of health sensor data based on the body surface;
        a second near-field antenna configured to communicate with the first near-field antenna in the single-use structure, wherein the second near-field antenna is configured to be conformally coupled to the body surface; and
        wherein the first near-field antenna and the second near-field antenna are aligned to an axis of the body surface circumference, wherein the alignment to the axis of the body surface circumference provides proper angular alignment between the first and second near-field antennas,
    wherein the single-use structure is wholly powered by a near-field signal from the re-useable structure.

2. The device of claim 1:
    wherein the body surface has a maximum cross-section; and
    wherein the first near-field antenna has at least one spatial dimension greater than or equal to the maximum cross-section.

3. The device of claim 1:
    wherein the first near-field antenna is configured to surround at least one of: the body surface, a waist, a torso, an arm, a leg, a lower body region, a wound, a chest, or a head.

4. The device of claim 1:
    wherein the first near-field antenna includes at least one of: an air core or a ferrite core.

5. The device of claim 1:
wherein a shape of the first near-field antenna is at least one of: a solenoid, a dipole, a closed shape, a spiral or a loop.

6. The device of claim 1:
wherein the first near-field antenna includes a detachable electrical coupling between a first and second antenna segments.

7. The device of claim 1:
wherein the first near-field antenna is embedded in at least one of: an item of clothing, a sock, an undergarment, a diaper, a bandage, a tape, a splint, a cast, a bed sheet, a cushion, or a covering.

8. The device of claim 1:
wherein at least one of the sensors is: a humidity sensor, a temperature sensor, a pressure sensor, a gas sensor, molecular sensor, a microbial sensor, a stress sensor, a position sensor, or a proximity sensor.

9. The device of claim 1:
wherein the re-useable structure further comprises a wireless antenna configured to transmit the set of health sensor data using at least one of: a wifi signal, a cellular signal, a Bluetooth signal, or a zigbee signal.

10. The device of claim 9:
wherein the re-useable structure is configured to transmit an alarm signal over the wireless antenna in response to a threshold value within the set of health sensor data.

11. The device of claim 1:
wherein the second near-field antenna is spatially positioned with respect to the first near-field antenna so as to maximize a coupling factor between the first and second near-field antennas.

12. The device of claim 1:
wherein the first near-field antenna has at least one spatial dimension greater than or equal to a cross-section of the body surface.

13. The device of claim 1, wherein a diameter of the first near-field antenna and the second near-field antenna is the same.

14. Health monitoring device, comprising:
a single-use structure comprising:
  a set of sensors configured to generate a set of health sensor data based on a body surface;
  a communications circuit configured to receive the set of health sensor data based on the body surface; and
  a first near-field antenna, coupled to the circuit, and configured to be conformally coupled to the body surface, wherein the first near-field antenna is located in a top part of the single-use structure, wherein the set of sensors and the first near-field antenna are externally powered passive circuits; and
a re-useable structure, wherein the re-usable structure is wearable, the re-usable structure comprising:
  a near-field reader configured to process the set of health sensor data based on the body surface, wherein the near-field reader is configured to be powered by a battery;
  a second near-field antenna configured to communicate with the first near-field antenna in the single-use structure, wherein the second near-field antenna is configured to be conformally coupled to the body surface, wherein the second near-field antenna is configured to be powered by the battery, wherein the first near-field antenna and the second near-field antenna are aligned to an axis of the body surface circumference, wherein the alignment to the axis of the body surface circumference provides proper angular alignment between the first and second near-field antennas; and
  wherein the single-use structure is wholly powered by a near-field signal from the re-useable structure.

15. The device of claim 14, wherein the body surface has a maximum cross-section, and wherein the first near-field antenna has at least one spatial dimension greater than or equal to the maximum cross-section.

16. The device of claim 14, wherein the first near-field antenna is configured to surround at least one of: the body surface, a waist, a torso, an arm, a leg, a lower body region, a wound, a chest, or a head.

17. The device of claim 14, wherein the second near-field antenna is spatially positioned with respect to the first near-field antenna so as to maximize a coupling factor between the first and second near-field antennas.

18. A method comprising:
generating, by a set of sensors of a single-use structure of a health monitoring device, a set of health sensor data based on a body surface;
receiving, by a communications circuit of the single-use structure, the set of health sensor data based on the body surface;
transmitting, by a first near-field antenna of the single-use structure, the set of health sensor data, the first near-field antenna configured to be conformally coupled to the body surface, wherein the set of sensors and the first near-field antenna are externally powered passive circuits; and
receiving, by a second near-field antenna of a re-useable structure of the health monitoring device the set of health sensor data from the first near-field antenna in the single-use structure, wherein the second near-field antenna is configured to be conformally coupled to the body surface, wherein the first near-field antenna and the second near-field antenna are aligned to an axis of the body surface circumference, wherein the alignment to the axis of the body surface circumference provides proper angular alignment between the first and second near-field antennas; and
processing, by a near-field reader of the re-useable structure, the set of health sensor data based on the body surface, wherein the re-usable structure is wearable, and wherein the single-use structure is wholly powered by a near-field signal from the re-useable structure.

19. The method of claim 18 further comprising:
transmitting, by a wireless antenna of the re-useable structure, the set of health sensor data, wherein the transmission uses at least one of: a wifi signal, a cellular signal, a Bluetooth signal, or a zigbee signal.

20. The method of claim 18 further comprising:
transmitting, by re-useable structure, an alarm signal over the wireless antenna in response to a threshold value within the set of health sensor data.

* * * * *